United States Patent [19]
Morley et al.

[11] Patent Number: 5,955,425
[45] Date of Patent: Sep. 21, 1999

[54] PARATHYROID HORMONE ANALOGUES FOR THE TREATMENT OF OSTEOPOROSIS

[75] Inventors: Paul Morley; Witold Neugebauer, both of Ottawa; Virginia J. S. Ross, Gloucester; James F. Whitfield, Ottawa; Gordon E. Willick, Orleans; Jean-René Barbier, Gatineau, all of Canada

[73] Assignee: National Research Council of Canada, Canada

[21] Appl. No.: 08/691,647

[22] Filed: Aug. 2, 1996

Related U.S. Application Data

[63] Continuation-in-part of application No. 08/262,495, Jun. 20, 1994, Pat. No. 5,556,940.

[51] Int. Cl.$^6$ .......................... A61K 38/29; C07K 14/635
[52] U.S. Cl. .............................. 514/11; 514/12; 530/317; 530/324
[58] Field of Search .................................. 530/317, 324, 530/345; 514/11, 12, 21

[56] References Cited

U.S. PATENT DOCUMENTS

| | | | |
|---|---|---|---|
| 4,587,046 | 5/1986 | Goodman et al. | 530/330 |
| 5,149,779 | 9/1992 | Chorev et al. | 530/317 |
| 5,434,246 | 7/1995 | Fukuda et al. | 530/324 |
| 5,556,940 | 9/1996 | Willick et al. | 530/317 |
| 5,582,995 | 12/1996 | Avruch et al. | 435/69.1 |
| 5,589,452 | 12/1996 | Krstenansky et al. | 514/12 |
| 5,670,483 | 9/1997 | Zhang et al. | 514/14 |
| 5,686,563 | 11/1997 | Kari | 530/326 |
| 5,717,062 | 2/1998 | Chorev et al. | 530/317 |
| 5,723,577 | 3/1998 | Dong | 530/324 |
| 5,747,456 | 5/1998 | Chorev et al. | 514/12 |

FOREIGN PATENT DOCUMENTS

| | | |
|---|---|---|
| 2269176 | 2/1994 | United Kingdom . |
| WO 94/07514 | 4/1994 | WIPO . |
| WO 96/40193 | 12/1996 | WIPO . |

OTHER PUBLICATIONS

Proceedings of 13th American Peptide Symposium Jun. 1993 pp. 556–558 Surewicz et al "Structure–function relationships in human parathyroid hormone: The Essential role of amphiphilic α–helix".

Biochemical and Biophysical Research Communications vol. 181, No. 1, 1991 pp. 481–485 Sung et al "Internal Ribosome–Binding Site Directs Expression of Parathyroid Hormone Analogue etc.".

J. of Biological Chemistry vol. 266, No. 5 Feb. 15, 1991 pp. 2831–2835 Sung et al "Specific Degenerate Condons . . . ".

Biochemical and Biophysical Research Communications vol. 171, No. 3, 1990 pp. 1105–1110 Chakravarthy et al "Parathyroid Hormone Fragament [3–34] Stimulates Protein Kinase C (PKC) . . . ".

Endocrinology vol. 130, No. 1 pp. 53–60 Jouishomme et al "The Protein Kinase–C Activation . . . " (1992).

J. of Bone and Mineral Research vol. 9, No. 8, 1994 pp. 1179–1189 Rixon et al "Parathyroid Hormone . . . ".

(List continued on next page.)

*Primary Examiner*—Jeffrey E. Russell
*Attorney, Agent, or Firm*—Nixon & Vanderhye

[57] ABSTRACT

This invention describes analogs of human parathyroid hormone which have increased activities in bone restoration, and increased bioavailabilities. The peptides described are derivatives of hPTH-(1–31) which have lactams formed for example, between either $Glu^{22}$ and $Lys^{26}$ or $Lys^{26}$ and $Asp^{30}$. In addition, the natural $Lys^{27}$ may be substituted by either a Leu or other hydrophobic residues, such as Ile, norleucine, Met, Val, Ala, Trp, or Phe. Typically, these analogs have enhanced abilities to stimulate adenylyl cyclase in rat osteosarcoma cells, and show increased activities in bone restoration, using the ovariectomized rat model. The analogs also show enhanced activities and bioavailabilities, as demonstrated by their hypotensive effects in the rat.

8 Claims, 6 Drawing Sheets

H₂N-Ser-Val-Ser-Glu-Ile-Gln-Leu-Met-His-Asn-Leu-Gly-Lys-His-Leu-Asn-Ser-Met-Glu-Arg-

Val-Glu-Trp-Leu-Arg-Lys-Leu-Leu-Gln-Asp-Val-NH₂

OTHER PUBLICATIONS

Biochemistry 1992, 31, pp. 2056–2063 Neugebauer et al "Structural Elements of Human Parathyroid . . . ".

Int. J. Peptide Protein Res. 43 1994 pp. 555–562 Neugebauer et al "Structure and protein kinase C . . . ".

Calcif Tissue Int (1996) 58:81–87 Whitfield et al "Stimulation of the Growth of Femoral Trabecular Bone . . . ".

Inst. Biological Sciences Oct. 1996 Barbier et al "Bioactivities and Secondary Structures . . . ".

Inst. Biological Sciences Whitfield et al Cyclization by a Specific Lactam Increases the Ability . . . (Not dated–in press).

Calcif Tissue Int (1997) 60:302–308 Whitfield et al "The Hypotensive Actions of Osteogenic . . . ".

Calcif Tissue Int (1997) 60:26–29 Whitfield et al "Comparison of the Ability of Recombinant Human . . . ".

Neugebauer et al Proceedings of the 22nd European Peptide Symposiu,m 1992, Switzerland Lactam, Analogues of a Human Parathyroid Hormone etc. pp. 395–396.

H₂N-Ser-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Lys-Leu-Gln-Asp-Val-COOH

Fig. 1

H₂N-Ser-Val-Ser-Glu-Ile-Gln-Leu-Met-His-Asn-Leu-Gly-Lys-His-Leu-Asn-Ser-Met-Glu-Arg-
Val-Glu-Trp-Leu-Arg-Lys-Leu-Leu-Gln-Asp-Val-NH₂

Fig. 2

H₂N-Ser-Val-Ser-Glu-Ile-Gln-Leu-Met-His-Asn-Leu-Gly-Lys-His-Leu-Asn-Ser-Met-Glu-Arg-
Val-Glu-Trp-Leu-Arg-Lys-Leu-Leu-Gln-Asp-Val-NH₂

Fig. 3

```
                           SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
         (A) LENGTH: 31 amino acids
         (B) TYPE: amino acid
         (D) TOPOLOGY: linear (ii) MOLECULE TYPE: protein (xi) SEQUENCE DESCRIPTION: SEQ ID NO: 1:

Ser Val Ser Glu Ile Gln Leu Met His Asn Leu Gly Lys His Leu
1               5                  10                  15

Asn Ser Met Glu Arg Val Glu Trp Leu Arg Lys Lys Leu Gln Asp Val
                20                  25                  30

(2) INFORMATION FOR SEQ ID NO: 2:

(i) SEQUENCE CHARACTERISTICS:
         (A) LENGTH: 31 amino acids
         (B) TYPE: amino acid
         (D) TOPOLOGY: linear (ii) MOLECULE TYPE: protein (xi) SEQUENCE DESCRIPTION: SEQ ID NO: 2:

Ser Val Ser Glu Ile Gln Leu Met His Asn Leu Gly Lys His Leu
1               5                  10                  15

Asn Ser Met Glu Arg Val Glu Trp Leu Arg Lys Leu Leu Gln Asp Val
                20                  25                  30

(2) INFORMATION FOR SEQ ID NO: 3:

(i) SEQUENCE CHARACTERISTICS:
         (A) LENGTH: 31 amino acids
         (B) TYPE: amino acid
         (D) TOPOLOGY: cyclic
```

(ii) MOLECULE TYPE: protein (ix) FEATURE:
         (D) OTHER INFORMATION:The side chains of Glu at position
             22 and Lys at position 26, are cyclised to form a lactum,
             and the sequence has a C-terminal amide (NH2) group.

(xi) SEQUENCE DESCRIPTION: SEQ ID NO: 3:

Ser Val Ser Glu Ile Gln Leu Met His Asn Leu Gly Lys His Leu
1               5                   10                  15

Asn Ser Met Glu Arg Val Glu Trp Leu Arg Lys Leu Leu Gln Asp Val
                20                  25                  30

(2) INFORMATION FOR SEQ ID NO: 4:

(i) SEQUENCE CHARACTERISTICS:
        (A) LENGTH: 31 amino acids
        (B) TYPE: amino acid
        (D) TOPOLOGY: cyclic (ii) MOLECULE TYPE: protein (ix) FEATURE:
         (D) OTHER INFORMATION: The side chains of Lys at position 26
             and Asp at position 30, are cyclised to form a lactum,
             and the sequence has a C-terminal amide (NH2) group.

(xi) SEQUENCE DESCRIPTION: SEQ ID NO: 4:

Ser Val Ser Glu Ile Gln Leu Met His Asn Leu Gly Lys His Leu
1               5                   10                  15

Asn Ser Met Glu Arg Val Glu Trp Leu Arg Lys Leu Leu Gln Asp Val
                20                  25                  30

(2) INFORMATION FOR SEQ ID NO: 5:

(i) SEQUENCE CHARACTERISTICS:
        (A) LENGTH: 34 amino acids
        (B) TYPE: amino acid
        (D) TOPOLOGY: linear (ii) MOLECULE TYPE: protein (xi) SEQUENCE DESCRIPTION:  SEQ ID NO: 5:

Ser Val Ser Glu Ile Gln Leu Met His Asn Leu Gly Lys His Leu
1               5                   10                  15

Asn Ser Met Glu Arg Val Glu Trp Leu Arg Lys Lys Leu Gln Asp
                20                  25                  30

Val His Asn Phe (2) INFORMATION FOR SEQ ID NO: 6:

(i) SEQUENCE CHARACTERISTICS:
        (A) LENGTH: 31 amino acids
        (B) TYPE: amino acid
        (D) TOPOLOGY: cyclic (ii) MOLECULE TYPE: protein (xi) SEQUENCE DESCRIPTION:  SEQ ID NO: 6:

Ser Val Ser Glu Ile Gln Leu Met His Asn Leu Gly Lys His Leu
1               5                   10                  15

Asn Ser Met Glu Arg Val Glu Trp Leu Arg Lys Lys Leu Gln Asp Val
                20                  25                  30

PARATHYROID HORMONE ANALOGUES FOR THE TREATMENT OF OSTEOPOROSIS

CROSS-REFERENCE TO RELATED APPLICATIONS

This application is a continuation-in-part of application Ser. No. 08/262,495, filed Jun. 20, 1994, now U.S. Pat. No. 5,556,940.

FIELD OF THE INVENTION

This invention relates to analogues of human parathyroid hormone, which have been found to be effective in the treatment of osteoporosis.

BACKGROUND OF THE INVENTION

Osteoporosis is a leading cause of disability in the elderly, particularly elderly women. It has recently been realized that human parathyroid hormone (hPTH) and certain analogues are stimulators of bone growth that are useful in the treatment of osteoporosis. Osteoporosis is a progressive disease which results in the reduction of total bone mass and increased bone fragility. This often results in spontaneous fractures of load-bearing bones and the physical and mental deterioration characteristic of immobilizing injuries. Postmenopausal osteoporosis is caused by the disappearance of estrogens which trigger a decade-long acceleration of bone turnover with an increased imbalance between resorption of old bone and formation of new bone. This results in thinning, increased porosity, and trabecular depletion of load-bearing bones. Osteoporosis is also associated with hyperthyroidism, hyperparathyroidism, Cushing's syndrome, and the use of certain steroidal drugs. Remedies historically have involved increase in dietary calcium, estrogen therapy, and increased doses of vitamin D, but mainly with agents such as antiresorptives that inhibit bone resorption by osteoclasts.

Parathyroid hormone (PTH) is produced by the parathyroid gland and is a major regulator of blood calcium levels. PTH is a polypeptide and synthetic polypeptides may be prepared by the method disclosed by Erickson and Merrifield, The Proteins, Neurath et al., Eds., Academic Press, New York, 1976, page 257, and as modified by the method of Hodges et al (1988) Peptide Research 1, 19 or by Atherton, E. And Sheppard, R. C. *Solid Phase Peptide Synthesis*, IRL Press, Oxford, 1989.

When serum calcium is reduced to below a normal level, the parathyroid gland releases PTH and the calcium level is increased by resorption of bone calcium, by increased absorption of calcium from the intestine, and by increased renal reabsorption of calcium from nascent urine in the kidney tubules. Although continuously infused low levels of PTH can remove calcium from the bone, the same low doses, when intermittently injected can actually promote bone growth.

Tregear, U.S. Pat. No. 4,086,196, described human PTH analogues and claimed that the first 27 to 34 amino acids are the most effective in terms of the stimulation of adenylyl cyclase in an in vitro cell assay. Rosenblatt, U.S. Pat. No. 4,771,124, disclosed the property of hPTH analogues wherein $Trp^{23}$ is substituted by amino acids phenylalanine, leucine, norleucine, valine, tyrosine, β-naphthylalanine, or α-naphthylalanine as a PTH antagonist. These modified hPTH analogues also have the 2 and 6 amino terminal acids removed, resulting in loss of most agonist activities when used to treat osteoporosis. These analogues were designed as inhibitors of PTH and RTH-related peptide. The analogues were claimed as possibly useful in the treatment of hypercalcemia associated with some tumors.

Pang et al, WO93/06845, published Apr. 15, 1993, described analogues of hPTH which involve substitutions of $Arg^{25}$, $Lys^{26}$, $Lys^{27}$ with numerous amino acids, including alanine, asparagine, aspartic acid, cysteine, glutamine, glutamic acid, glycine, histidine, isoleucine, leucine, methionine, phenylalanine, proline, serine, threonine, tryptophan, tyrosine, or valine. These are claimed, with no supporting data from animal or human trials, to be effective in the treatment of osteoporosis with minimal effects on blood pressure and smooth muscle.

PTH operates through activation of two second messenger systems, $G_s$-protein activated adenylyl cyclase (AC) and $G_q$-protein activated phospholipase $C_\beta$. The latter results in a stimulation of membrane-bound protein kinase Cs (PKC) activity. The PKC activity has been shown to require PTH residues 29 to 32 (Jouishomme et al (1994) *J. Bone Mineral Res.* 9, (1179–1189). It has been established that the increase in bone growth, i.e. that effect which is useful in the treatment of osteoporosis, is coupled to the ability of the peptide sequence to increase AC activity. The native PTH sequence has been shown to have all of these activities. The hPTH-(1–34) sequence is typically shown as (A):

```
    1                5                  10                      A
    |                |                  |
    Ser Val Ser Glu Ile Gln Leu Met His Asn Leu Gly Lys His   (SEQ ID NO:5)

15                   20                 25
    |                    |                  |
    Leu Asn Ser Met Glu Arg Val Glu Trp Leu Arg Lys Lys Leu

30
    |
    Gln Asp Val His Asn Phe-OH
```

The following linear analogue, hPTH-(1–31)-NH$_2$, for which data is included in Table 1, below, has only AC-stimulating activity and has been shown to be fully active in the restoration of bone loss in the ovariectomized rat model (Rixon, R. H. et al (1994) *J. Bone Miner. Res.* 9, 1179–1189; Whitfield et al (1996), *Calcified Tissue Int.* 58, 81–87; Willick et al, U.S. Pat. No. 5,556,940, issued Sep. 17, 1996:

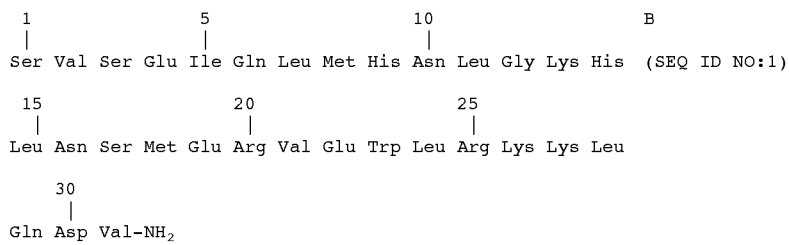

The above molecule, B, may have a free carboxyl ending instead of the amide ending illustrated. A version of molecule B, where Lys is replaced with Leu, is illustrated by SEQ ID NO:2. The sequence listing includes as a feature the location of the cyclization and the C-terminal amide (—NH$_2$) ending.

It is an object of the present invention to produce new PTH analogues with greater metabolic stability, increased bone restoration activity, increased AC activity, and minimal clinical side effects.

BRIEF SUMMARY OF THE INVENTION

According to one feature of the present invention, lactams are formed for example, by cyclisation involving the coupling of the side-chains of Glu$^{22}$ and Lys$^{26}$, or of the side-chains Lys$^{26}$ and Asp$^{30}$, of molecule B, in which Lys$^{27}$ may be replaced by a Leu (SEQ ID NO:3 and 4) or by various other hydrophobic residues, and which has either a C-terminal free amide ending as illustrated above, or has a C-terminal free carboxyl ending. The respective cyclized versions of the corresponding natural Lys$^{27}$ analogue are identified by SEQ. ID NO:6. Such substitutions include ornithine, citrulline, α-aminobutyric acid, or any linear or brached α-amino aliphatic acid, having 2–10 carbons in the side chain, any such analogue having a polar or charged group at the terminus of the aliphatic chain. Example of polar or charged groups include; amino, carboxyl, acetamido, guanido and ureido. Ile, norleucine, Met, and ornithine are expected to be the most active.

This results in a stabilization of an α-helix in the receptor-binding region of the hormone. This has been confirmed by examination of the circular dichroism spectrum of the lactam analogues, as compared to the circular dichroism spectrum of the linear molecule, [Leu$^{27}$]-hPTH-(1–31)—NH$_2$. Circular dichroism spectra are highly sensitive to the presence of α-helical secondary structure, and the technique has been used to demonstrate the presence of α-helix in hPTH fragments (Neugebauer et al (1991) *Biochemistry* 31, 2056–2063). Furthermore, the stabilization of α-helix on formation of the above mentioned lactams in hPTH-(20–34)—NH$_2$ has been shown (Neugebauer et al (1994) *Int. J. Protein Peptide Res.* 43, 555–562). There is a potential amphiphilic α-helix between residues 21 and 31 of hPTH-(1–31)—NH$_2$, and data has been presented showing that the hydrophobic face of this helix interacts with the PTH receptor (Neugebauer, W. (1995) et al *Biochemistry 34, 8835–8842;* Gardella, T. J. et al (1993), *Endocrinology 132, 2024–2030*).

The invention features the formation of a lactam, for example, between either residues Glu$^{22}$ and Lys$^{26}$, or Lys$^{26}$ and Asp$^{30}$. It will be appreciated by those skilled in the art that other cyclisations are also possible such as between Lys$^{26}$ and Asp$^{30}$ and as between Glu$^{22}$ and Lys$^{27}$. The substitution of Leu for the Lys$^{27}$ results in a more hydrophobic residue on the hydrophobic face of the amphiphilic helix. This resulted in increased adenylyl cyclase stimulating activity in the ROS cell line. It will be appreciated by those skilled in the art that other such substitutions would likely result in analogues with the same or increased activities. These hydrophobic substitutions include residues such as Met or norleucine. The combined effect of substitution and either lactam formation is expected to stabilize the α-helix and increase bioactivity, and to protect this region of the molecule from proteolytic degradation. The presence of the amide at the C-terminus is further expected to protect the peptide against exoproteolytic degradation (Leslie, F. M. and Goldstein, A. (1982) *Neuropeptides* 2, 185–196).

The lactams according to the invention may be prepared by known procedures described below, and may be used for stimulating bone growth, for restoring bone, and for the promotion of bone healing in various circumstances, such as in the treatment of osteoporosis and normal fractures.

BRIEF DESCRIPTION OF THE DRAWINGS

FIG. 1 shows the structure of natural human PTH, residues 1–31 (SEQ ID NO: 1);

FIG. 2 shows the structure of [Leu$_{27}$]cyclo(Glu$^{22}$-Lys$^{26}$) hPTH-(1–31)—NH$_2$ (SEQ ID NO: 3);

FIG. 3 shows the structure of [Leu$_{27}$]cyclo(Lys$^{26}$-Asp$^{30}$) hPTH-(1–31)—NH$_2$ (SEQ ID NO: 4);

PREPARATION OF HORMONE ANALOGUES

Figure 4:
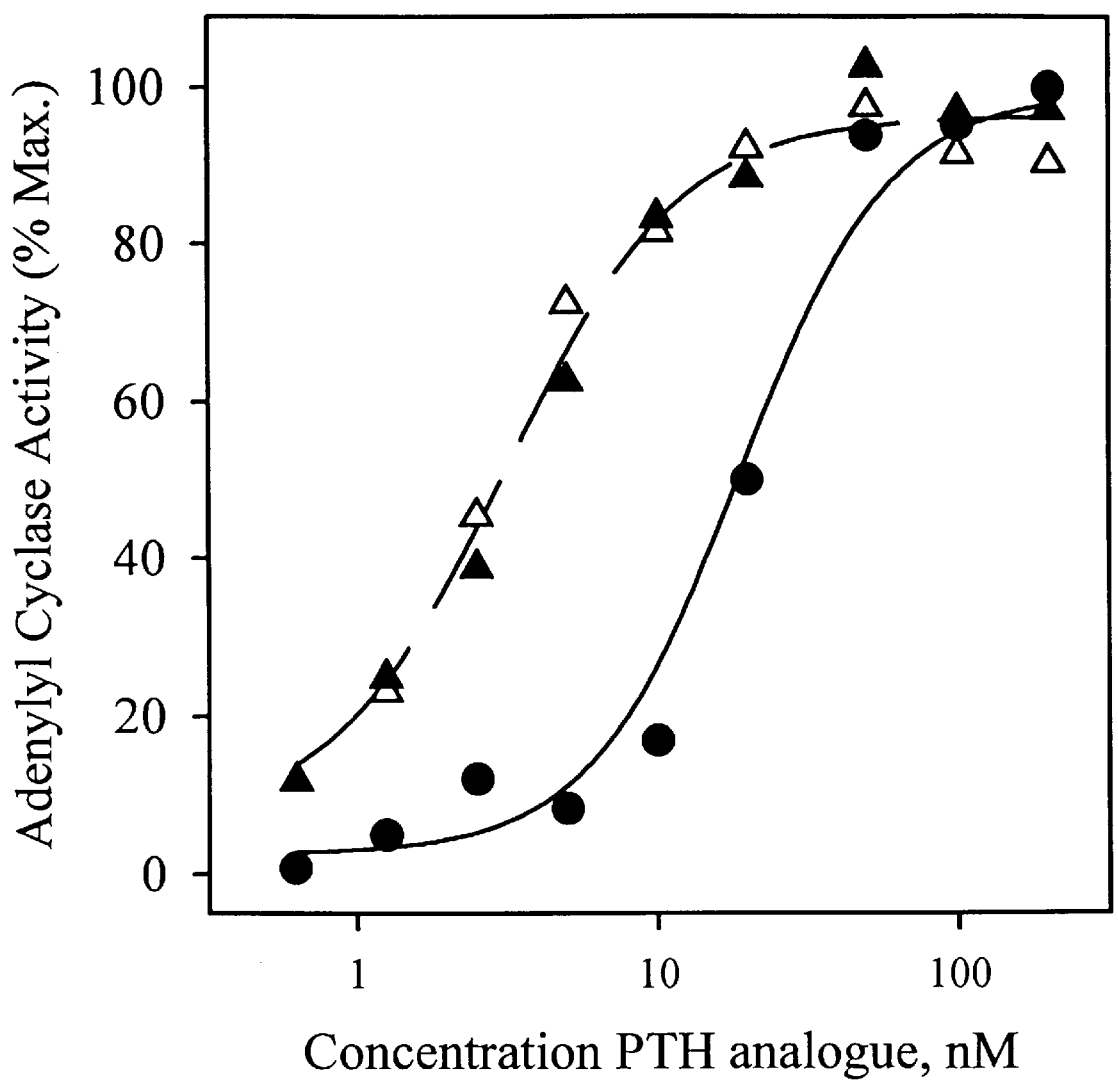
FIG. 4 shows the activities of the analogues according to the invention in adenylyl cyclase stimulation of ROS 17/2 cells.

The technique of solid phase peptide synthesis developed by R. B. Merrifield ("Solid-Phase Peptide Synthesis", Advances in Enzymology 32, 221–296, 1969), incorporated herein by reference, is widely and successfully used for the synthesis of polypeptides such as parathyroid hormone. The strategy is based on having the carboxyl-terminus amino acid of the peptide attached to a solid support. Successive amino acids are then added in high yield. The α-amino group is protected in such a way that this protecting group can be removed without removal of the peptide from the solid support. The chemistry used here involves a modification of the original Merrifield method, referred to as the Fmoc approach. The Fmoc (fluorenylmethoxycarbonyl) group can be removed by mild alkaline conditions, which leaves the alkali stable side-chain protecting groups and the link to the support untouched. This technique is described by E. Atherton and R. C. Sheppard, "Solid Phase Peptide Synthesis: a Practical Approach", IRL Press, New York, N.Y., incorporated herein by reference.

EXAMPLE 1

Synthesis and Purification of Linear hPTH-(1–31)-amide Analogues

The α-amino groups of the amino acids were protected by 9-fluorenyl-methoxycarbonyl (Fmoc) during coupling. Couplings were performed with a mixture of hydroxybenzotriazole (HOBt), 2-(1H-benzotriazole-1-yl)1,1,3,3-tetramethyluronium tetrafluoroborate (TBTU), and diisopropylethylamine (DIPEA). A 4-fold excess of activated amino acids was used with double coupling on addition of the Asn, Gln, His, Val, and Ile residues. The coupling times for Arg and Gly additions were increased from 30 to 60 minutes. Coupling of the first residue (Val$^{31}$) to the support (Tentagel R, Rapp Polymere, Tubingen, Germany) was performed manually. All other steps were performed on a PerSeptive Biosystems Model 9050 Plus automated peptide synthesizer. Side chain protections were as follows: Arg (2,2,5,7,8-pentamethylchroman-6-sulfonyl); Glu, Asp, and Ser (t-butyl); His, Gln, and Asn (trityl); Trp (t-butyloxycarbonyl).

After Fmoc removal from the N-terminal Ser, the peptide resin was washed with DCM, then cleaved from the resin by shaking with 7.5 ml of reagent K (6.19 ml TFA, 0.38 ml each of water, 90% phenol/water, and thioanisole, and 0.19 ml of 1,2-ethanedithiol) for 4 hr at 20° C. The cleaved peptide mixture was removed by filtration, and precipitated by addition to t-butyl-methylether. The precipitate was collected by centrifugation, washed 2× with t-butyl-methylether, then dried by vacuum centrifugation.

The crude product was dissolved in 14 ml of 15% acetonitrile/water, 0.1% TFA and chromatographed on a Vydac C$_{18}$-column (10 μ, 1×25 cm). The product was eluted with a 1%/min. gradient of acetonitrile (14–40%) in 0.1% TFA in water. The purity of the final product was estimated by analytical HPLC on a Vydac C$_{18}$ column (10 μ, 0.4×25 cm), and by molecular mass assay on an electrospray mass spectrometer (VG Quattro). The data for hPTH-(1–31)—NH$_2$ so formed, is given in Table 1 below.

EXAMPLE 2

Synthesis and Purification of Cyclic Analogues

[Leu$^{27}$]cyclo(Glu$^{22}$-Lys$^{26}$)-hPTH-(1–31)—NH$_2$. This peptide was synthesized as described for Example 1, with Lys-Alloc and Glu-OA11 substituted at position 26 and 22, respectively. After the addition of Fmoc-Ser$^{17}$, the peptide-resin was removed from the column to a reaction vial (Minivial, Applied Science), suspended in 1.7 ml of a solution of tetrakis(triphenylphosphine)palladium(0) (0.24 mmol), 5% acetic acid and 2.5% N-methylmorpholine (NMM) in dichloromethane (DCM) under argon, then shaken at 20° C. for 6 hr to remove the allyl and alloc protecting groups (Solé, N. A. et al (1993) In Peptides: Chemistry, Structure, and Biology, Smith, J. And Hodges, R. (Eds), ESCOM pp. 93–94, incorporated herein by reference). The peptide resin was then washed with 0.5% diethyldithiocarbamate (DEDT), 0.5% NMM in DMF (50 ml), followed by DMF (50 ml) and DCM (50 ml). The peptide (0.06 mmol) was cyclized by shaking with 0.06 mmol of 1-hydroxy-7-azabenzotriazole (HOAt)/0.12 mmol NMM in 2 ml DMF for 14 h at 20° C. (Carpino, L. A. (1993) J. Am. Chem. Soc. 115, 4397–4398). The peptide-resin was filtered, then washed once with DMF, repacked into the column, and washed with DMF until bubbles were removed from the suspension. The remaining synthesis was carried out as with Example 1 except that the N-terminal Fmoc group was not removed. The Fmoc-peptide was cleaved from the resin with reagent K as described above. The HPLC was carried out as in Example 1, with the Fmoc group removed prior to the final HPLC.

Analogue [Leu$^{27}$]cyclo(Lys$^{26}$-Asp$^{30}$)-hPTH-(1–31)—NH$_2$ was prepared in an analogous manner.

EXAMPLE 3

Adenylyl Cyclase Assays

The ability of the hPTH analogues to bind to receptors and activate the adenylyl cyclase coupled signalling mechanism was determined on a differentiation-competent osteoblast-like ROS 17/2 rat osteosarcoma (ROS) cell line. This activity is known to be tightly coupled to the ability of the analogue to restore bone mass in the ovariectomized rat. Adenylyl cyclase-stimulating activity was estimated by prelabelling the cellular ATP pool with [$^3$H]-adenine and then measuring the amount of [$^3$H]-cyclic AMP produced from the [$^3$H]-ATP during the first 10 min of exposure to a particular analogue. This was based on the procedure described by Whitfield et al, J. Cellular Physiology 150, 299–303, 1992, incorporated herein by reference.

The adenylyl cyclase results are expressed in Table 2 below as the concentration necessary to express a half-maximal increase in the AC activity. The data is also displayed in FIG. 4. In FIG. 4, the closed circles show the adenylyl cyclase-stimulating activity of hPTH-(1–31)NH$_2$, and the activities of [Leu$^{27}$]cyclo(Glu$^{22}$-Lys$^{26}$)-hPTH (1–31)—NH$_2$ and [Leu$^{27}$]cyclo(Lys$^{26}$-Asp$^{30}$)-hPTH-(1–31)—NH$_2$ are shown by open and closed triangles, respectively.

EXAMPLE 4

Determination of Anabolic Activities of hPTH Analogues with Ovariectomized Rat Model A full description of the protocol is given in Rixon et al, J. Bone & Mineral Research 9, 1179–1189, 1994 and Whitfield et al Calcif. Tissue Int. 58, 81–87, 1996 incorporated herein by reference. Normal, Sham-OVX (ovariectomized), and OVX Sprague-Dawley rats (3 months-old; 255–260 g) were purchased from Charles River Laboratories (St.Constant, QC). The rats were randomized into groups of 8 animals which received Purina rat chow and water ad libitum. There were no unscheduled deaths. The animals received 6, once-daily subcutaneous injections/ week starting at the end of the second week after OVX. and ending at the end of the 8th week after OVX (i.e., 36 injections ). Eight Sham-OVX and 8 OVX controls rats received 36 injections of vehicle (0.15 M NaCl containing 0.001 N Hcl) while 8 OVX rats received 0.6 n mole of fragment in vehicle/100 g of body weight). At the end of the 8th week after OVX, femurs were removed isolated, cleaned, and cut in half at mid-diaphysis and the proximal half was discarded. After removing the epiphysis, each half-femur was split lengthwise into two parts and the bone marrow was flushed out.

The bone-building potencies of the fragments were assessed from the changes in the mean thicknesses (area/perimeter) of the trabeculae in the distal half-femurs from the variously treated animals. To measure mean trabecular thickness, the two demineralized half-femurs from each rat were dehydrated and embedded in paraffin. Longitudinal, 10 $\mu$m sections from the middle plane of each bone were cut and then stained with Sanderson's rapid bone stain (Surgipath Medical Industries, Inc., Winnipeg, MB, Canada). The mean trabecular thickness was measured using a M4 imaging system and bone morphometric software from Imaging Research Inc.,( St. Catherines, ON, Canada).

Figure 5:
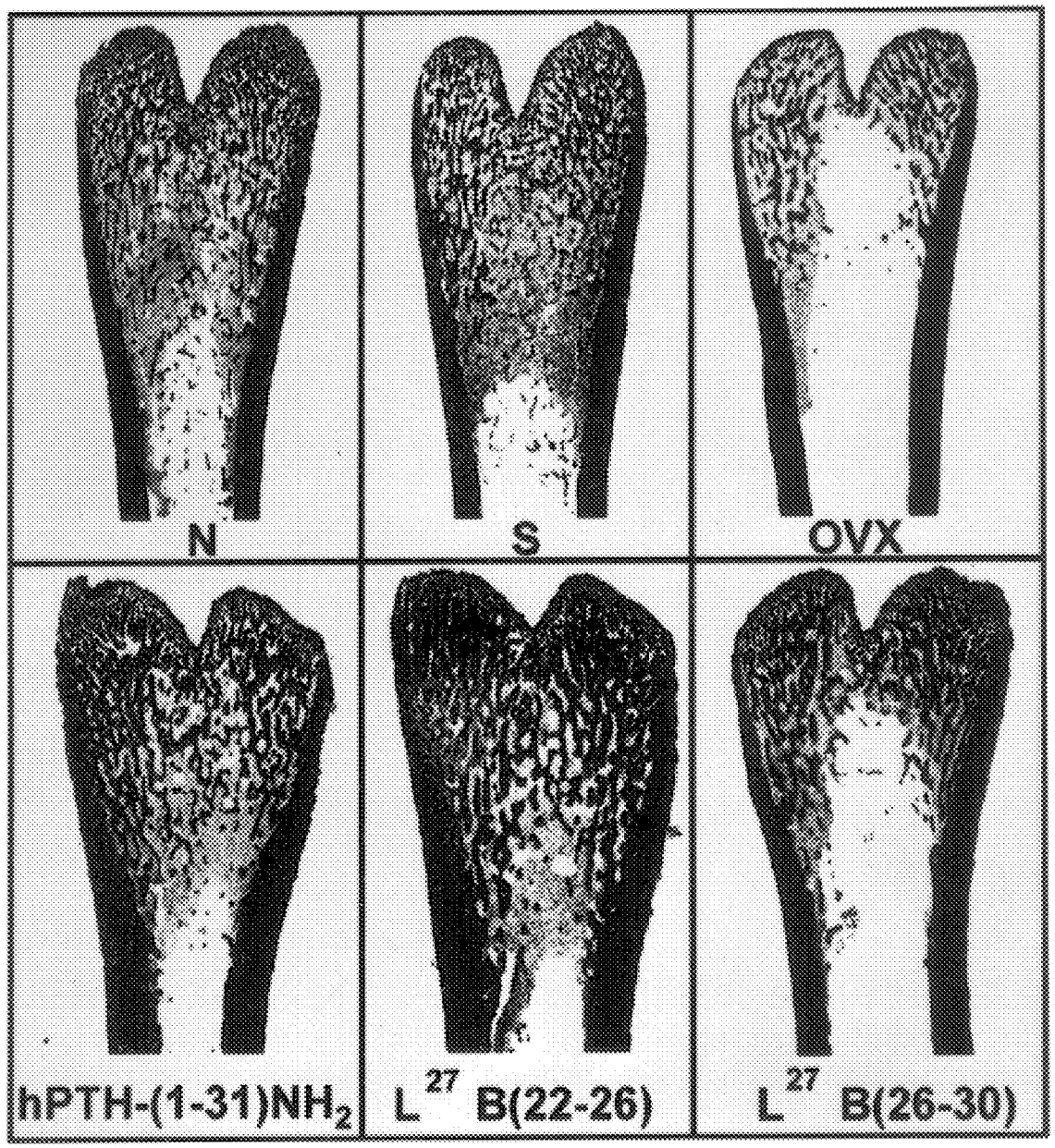
FIG. 5 shows representative histological sections of bones prepared at the end of 8 weeks after OVX, illustrating the different abilities of hPTH-(1–31)NH$_2$ and its lactam derivatives to prevent bone loss and to stimulate bone growth in ovariectomized (OVX) Sprague-Dawley rats.
Figure 7:
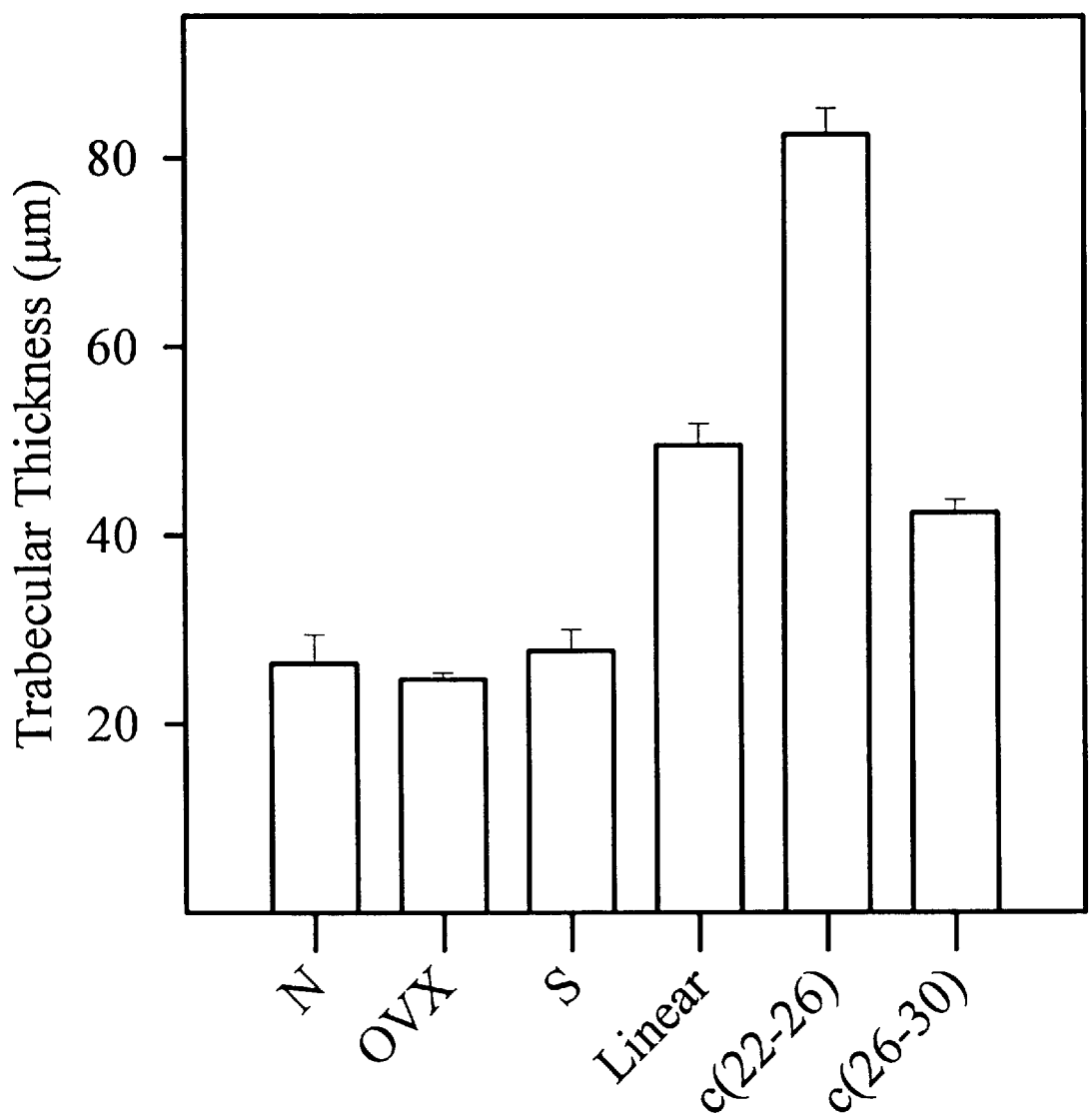
FIG. 7 shows trabecular thicknesses of rat femurs for normal, ovariectomized (OVX), sham, and animals treated with hPTH-(1–31)—NH$_2$, [Leu$^{27}$]cyclo(Glu$^{22}$-Lys$^{26}$)-hPTH-(1–31)—NH$_2$, and [Leu$^{27}$]cyclo(Lys$^{26}$-Asp$^{30}$)-hPTH-(1–31)—NH$_2$.

Representative histological sections of bones prepared at the end of 8 weeks after OVX are shown in FIG. 5. The results are further presented in the form of a bar graph in FIG. 7. Each graph shows the values for trabecular thickness of the normal, ovariectomized (OVX), sham, hPTH-(1–31)—NH$_2$, [Leu$^{27}$]cyclo(Glu$^{22}$-Lys$^{26}$)-hPTH-(1–31)—NH$_2$, and [Leu$^{27}$]cyclo(Lys$^{26}$-Asp$^{30}$)-hPTH-(1–31)—NH$_2$. [Leu$^{27}$]cyclo(Glu$^{22}$-Lys$^{26}$)-hPTH-(1–31)—NH$_2$ shows an especially superior activity compared to the linear analogue, hPTH-(1–31)—NH$_2$. This linear analogue has been shown to be fully active in bone restoration, but uses only one cellular signalling (the AC-activated) pathway. Thus, these cyclic analogues, like their linear analogue, are expected to have fewer undesired clinical side-effects than their longer counterparts, such as hPTH-(1–34) or hPTH-(1–84), which activate both cellular signalling mechanisms.

EXAMPLE 5

Bone Restoration by hPTH Analogues of Rats with Severely Depleted Trabecular Bone.

Figure 6:
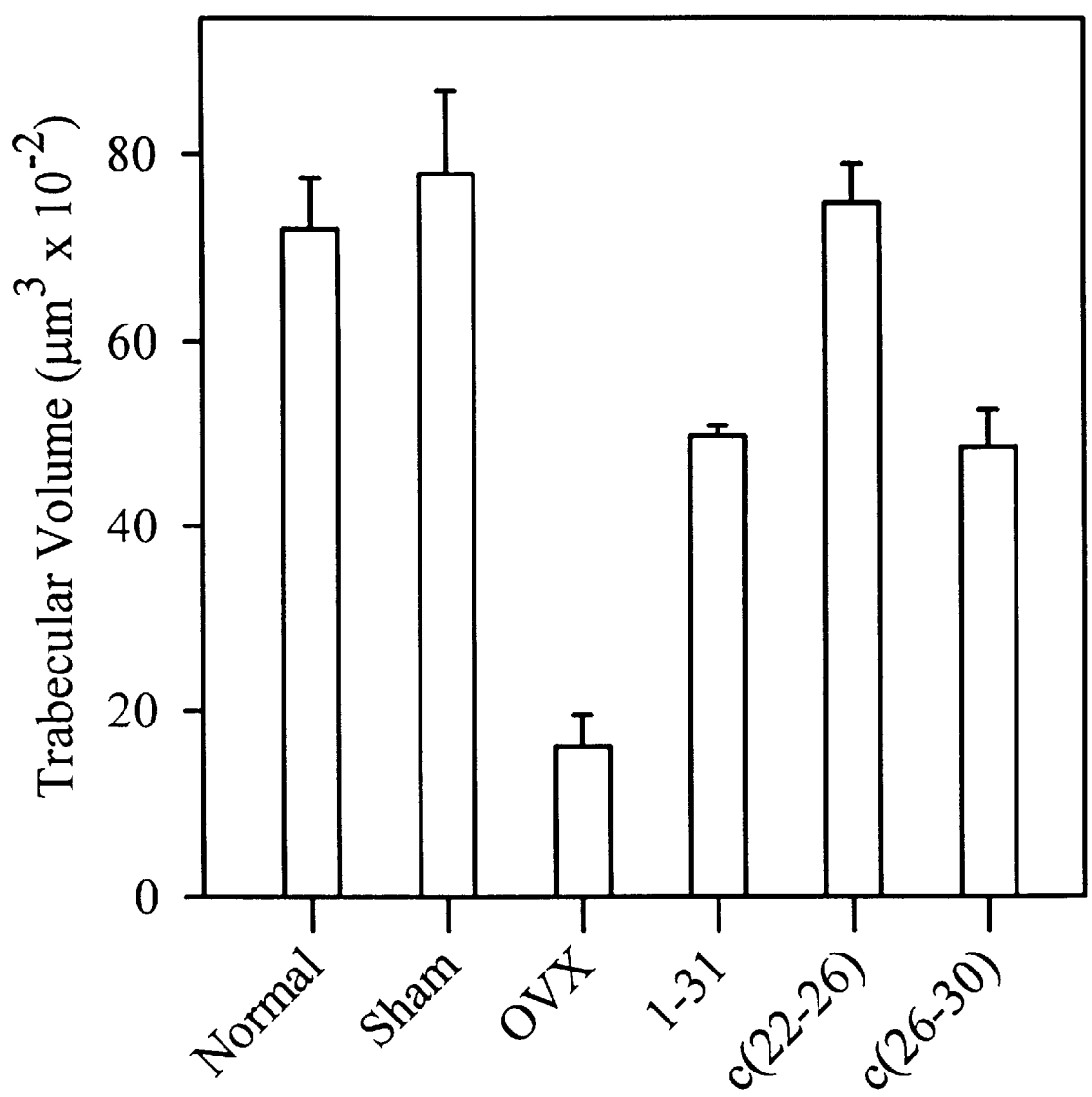
FIG. 6 shows the trabecular bone volume of control animals and hPTH analogue treated animals for rats initially severely depleted of bone. Treatment of the animals began 9 weeks after OVX. [Leu$^{27}$]cyclo[Glu$^{22}$-Lys$^{26}$]hPTH-(1–31)—NH$_2$ was the most effective of the fragments, restoring the bones to the values in normal control rats.

In this second example of bone restoration, the abilities of the lactam fragments to restore severely depleted trabecular bone are compared. In this experiment, the 6-week program of once-daily injections of 0.6 nmole of peptide/100 g of body weight of young sexually mature rats was delayed until the end of the 9th week after OVX. At this time, 75% of their trabecular bone had been lost. As can be seen in FIG. 6, [Leu$^{27}$]cyclo[Glu$^{22}$-Lys$^{26}$]-hPTH-(1–31)NH$_2$ was the most effective of the fragments. It restored the trabecular bone volume to the values in normal control rats.

EXAMPLE 6

Hypotensive Effects of hPTH Analogues

Figure 8:
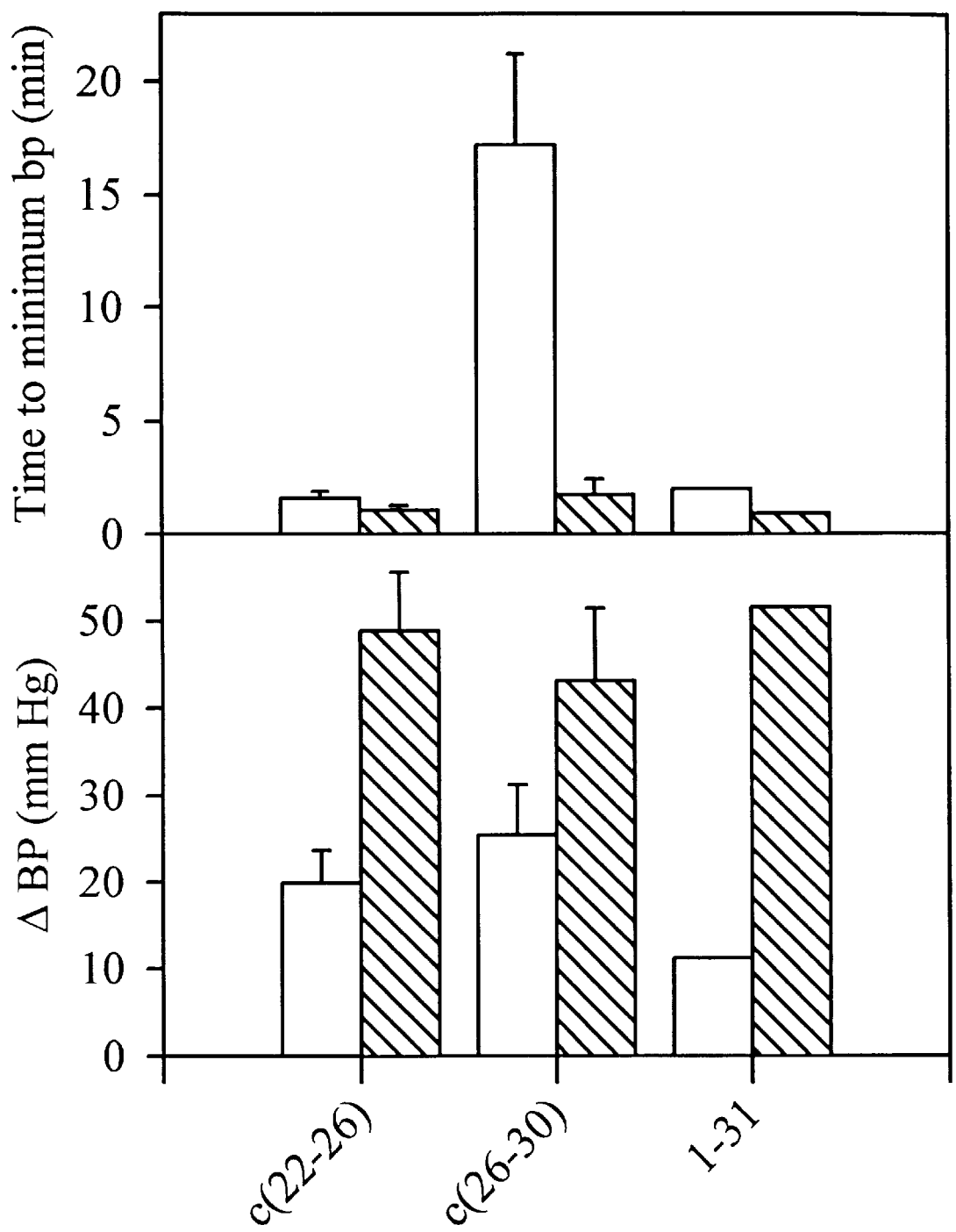
FIG. 8 shows the maximum drop in blood pressure and time to maximum drop in blood pressure on addition of 0.8 nmol/100 g dose of hPTH-(1–31)—NH$_2$, [Leu$^{27}$]cyclo (Glu$^{22}$-Lys$^{26}$)hPTH-(1–31)—NH$_2$, or [Leu$^{27}$]cyclo(Lys$^{26}$-Asp$^{30}$)hPTH-(1–31)—NH$_2$. Peptides were administered either subcutaneously (open bar) or intravenously (hatched bar).

Female Sprague-Dawley rats (weighing over 290 g) were anaesthetized with intraperitoneally injected sodium pentobarbital (65 mg/kg body weight). Rectal temperature was monitored with a YSI402 thermistor (Yellow Springs Instrument Co., Inc. Yellow Springs, Ohio) and maintained between 36.0 and 38.5° C. throughout the experiment. Ear pinna temperature was also monitored using a YSI banjo thermistor. The tail artery was exposed and cannulated with a Jelco 25-gIV catheter (Johnson and Johnson Medical Inc., Arlington, Tex.) and connected to a Statham pressure transducer, the signals from which were recorded digitally with a Biopac Systems MP100 Monitor (Harvard Instruments, Saint Laurent, QC, Canada). For intravenous injection of PTH or one of its fragments, a femoral vein was also exposed. After surgery, the rat was allowed to stabilize for 8 min after which PTH or one of its fragments (dissolved in acidified saline containing 0.001 N HCl) was injected into the femoral vein or under the skin of the abdomen. Data were collected for 12 min after intravenous injection or for 22 min after subcutaneous injection. FIG. 8 shows the maximum drop in blood pressure and time to maximum drop on addition of 0.8 nmol/100 g dose of [Leu$^{27}$]cyclo(Glu$^{22}$-Lys$^{26}$)hPTH-(1–31)—NH$_2$ or [Leu$^{27}$]cyclo(Lys$^{26}$-Asp$^{30}$)hPTH-(1–31)—NH$_2$ for administration by either subcutaneous (open bar) or intravenous (hatched bar) route. The [Leu$^{27}$]cyclo(Glu$^{22}$-Lys$^{26}$)hPTH-(1–31)—NH$_2$ analogue shows increased bioavailability, as compared to [Leu$^{27}$]cyclo(Lys$^{26}$-Asp$^{30}$)hPTH-(1–31)—NH$_2$. This is indicated by the much shorter time needed to drop to the minimum bp after subcutaneous injection. Both cyclic analogues show enhanced hypotensive effects when injected subcutaneously, when compared to hPTH-(1–31)—NH$_2$. Thus, each cyclic lactam analogue, when injected subcutaneously, is expected to have more desirable properties than the linear counterpart. These include greater bioavailabilities, resulting from enhanced resistance to proteases and/or increased ability to be transported from lipidic environments. The latter could be due to the stabilization of the amphiphilic helix near the C-terminus of the hormone.

The analogues of the present invention may be administered to a warm-blooded mammal, in need thereof, particularly a human, by parenteral, topical, or rectal administration, or by inhalation. The analogues may be conventionally formulated in a parenteral dosage form compounding about 1 to about 300 mg per unit of dosage with a conventional vehicle, excipient, binder, preservative, stabilizer, color, agent or the like as called for by accepted pharmaceutical practice.

For parenteral administration, a 1 to 2 ml painless subcutaneous injection through an ultra-fine 30-guage syringe needle would need to be given no more than once daily, for one to 2 years, depending on the severity of the disease. The injected material would contain one of the present invention in an aqueous, isotonic, sterile solution or suspension (optionally with a preservative such as phenol or a solubilizing agent such as ethylenediamine tetraacetic acid (EDTA)). Among the acceptable vehicles and solvents that may be employed are water, mildly acidified water, Ringer's solution and isotonic sodium chloride solution. In addition, sterile, fixed oils are conventionally employed as a solvent or suspending medium. Synthetic monoglycerides, diglycerides, fatty acids (such as oleic acid) find use as a fixed oil in the preparation of injectables.

For rectal administration, the analogues of the present invention can be prepared in the form of suppositories by mixing with a suitable non-irritating excipient such as cocoa butter or polyethylene glycols.

For topical use, the anlaogues of the present invention can be prepared in the form of ointments, jellies, solutions, suspensions or dermal adhesive patches.

The daily dose should not have to exceed 0.05 mg/kg of body weight, or about 3.5 mg/70 kg human, depending on the activity of the specific compound, the age, weight, sex, and conditions of the subject being treated. As would be well known, the amount of active ingredient that may be combined with the carried materials to produce a single dosage will vary depending upon the host treated and the particular mode of administration.

TABLE 1

Molecular Masses of Peptide Analogues

| SEQ ID | Analogue | Mass (determined) | Mass (expected) (M + 1) |
|---|---|---|---|
| 1 | hPTH-(1–31)-NH$_2$ | 3717.77 (±0.13) | 3717.14 |
| 3 | [Leu$^{27}$]cyclo(Glu$^{22}$—Lys$^{26}$)-hPTH-(1–31)-NH$_2$ | 3685.46 (±0.46) | 3685.12 |
| 4 | [Leu$^{27}$]cyclo(Lys$^{26}$—Asp$^{30}$)-hPTH-(1–31)-NH$_2$ | 3685.61 (±0.36) | 3685.12 |

TABLE 2

AC Activities of Peptide Analogues

| SEQ ID | Analogue | Concentration, nM (Half-maximal activity) |
|---|---|---|
| 2 | [Leu$^{27}$]-hPTH-(1–31)-NH$_2$ | 13 |
| 3 | [Leu$^{27}$]cyclo(Glu$^{22}$—Lys$^{26}$)-hPTH-(1–31)-NH$_2$ | 3 |
| 4 | [Leu$^{27}$]cyclo(Lys$^{26}$—Asp$^{30}$)-hPTH-(1–31)-NH$_2$ | 3 |

We claim:

1. A human parathyroid hormone hPTH-(1–31) analogue in which position 27 is Leu, Ile, Nle or Met and which has been cyclized between $Glu^{22}$ and $Lys^{26}$ to form a lactam.

2. An analogue according to claim 1, having either a free amide C-terminal ending or a free carboxyl C-terminal ending.

3. An analogue according to claim 1, having the SEQ ID NO:3.

4. A composition for administration to a warm-blooded animal comprising a human parathyroid hormone hPTH-(1–31) analogue according to claim 1 in association with a pharmaceutically acceptable carrier or excipient.

5. A method of treating osteoporosis in a warm-blooded animal comprising administering to an animal in need of same a therapeutically effective amount of the human parathyroid hormone hPTH-(1–31) analogue according to claim 1.

6. A human parathyroid hormone hPTH-(1–31) analogue in which position 27 is Leu and which has been cyclized between $Glu^{22}$ and $Lys^{26}$ to form a lactam.

7. A composition for administration to a warm-blooded animal comprising a human parathyroid hormone hPTH-(1–31) analogue according to claim 6 in association with a pharmaceutically acceptable carrier or excipient.

8. A method of treating osteoporosis in a warm-blooded animal comprising administering to an animal in need of same a therapeutically effective amount of the human parathyroid hormone hPTH-(1–31) analogue according to claim 6.

* * * * *

UNITED STATES PATENT AND TRADEMARK OFFICE

CERTIFICATE OF CORRECTION

PATENT NO. : 5,955,425
DATED : September 21, 1999
INVENTOR(S) : MORLEY ET AL.

It is certified that error appears in the above-identified patent and that said letters patent is hereby corrected as shown below:

Front page format at [75] should read:

--Inventors: Paul Morley; Witold Neugebauer; James F. Whitfield, three of Ottawa; Gordon E. Willick, Orleans; Jean-René Barbier, Gatineau, all of Canada--

Signed and Sealed this

First Day of August, 2000

*Attest:*

Q. TODD DICKINSON

*Attesting Officer*     *Director of Patents and Trademarks*

UNITED STATES PATENT AND TRADEMARK OFFICE
CERTIFICATE OF CORRECTION

PATENT NO. : 5,955,425
DATED : September 21, 1999
INVENTOR(S) : Paul Morley et al.

It is certified that error appears in the above-identified patent and that said Letters Patent is hereby corrected as shown below:

Title page,
Item [63], delete
"Related U.S. Application Data
Continuation-in-part of application No. 08/262,495, Jun. 20, 1994, Pat. No. 5,556,940.".

Column 1,
Lines 4-9, delete "Cross-Reference to Related Applications
This application is a continuation-in-part of application Ser. No. 08/262,495, filed Jun. 20, 1994, now U.S. Pat. No. 5,556,940.".

Column 3,
Line 38, "Example" should read -- Examples --.
Line 44, "spectrum" should read -- spectra --.

Column 5,
Line 4, "carboxyl-terminus" should read -- carboxy-terminal --.

Column 6,
Line 46, "is" should read -- are --.

Column 8,
Line 63, -- and -- should be inserted between "the specific compound," and "the age, weight, sex...".

Signed and Sealed this

Twenty-first Day of February, 2006

JON W. DUDAS
*Director of the United States Patent and Trademark Office*